(12) United States Patent
Salerno et al.

(10) Patent No.: US 7,808,641 B2
(45) Date of Patent: Oct. 5, 2010

(54) INTERACTIVE VARIABLE PATHLENGTH DEVICE

(75) Inventors: Mark Salerno, Cranford, NJ (US); Tsung Shih, Basking Ridge, NJ (US); Craig Harrison, Basking Ridge, NJ (US)

(73) Assignee: C Technologies Inc., Bridgewater, NJ (US)

( * ) Notice: Subject to any disclaimer, the term of this patent is extended or adjusted under 35 U.S.C. 154(b) by 295 days.

(21) Appl. No.: 12/100,467

(22) Filed: Apr. 10, 2008

(65) Prior Publication Data

US 2009/0027678 A1       Jan. 29, 2009

Related U.S. Application Data

(60) Provisional application No. 60/923,179, filed on Apr. 13, 2007.

(51) Int. Cl.
    *G01N 21/00* (2006.01)
(52) U.S. Cl. ...................................... 356/440
(58) Field of Classification Search .......... 356/335–344
    See application file for complete search history.

(56) References Cited

U.S. PATENT DOCUMENTS

| | | | | |
|---|---|---|---|---|
| 3,309,775 A | * | 3/1967 | Vieregge ................... 33/810 |
| 4,291,988 A | * | 9/1981 | Dixon et al. ................ 356/437 |
| 4,643,580 A | | 2/1987 | Gross et al. |
| 4,805,623 A | | 2/1989 | Jobsis |
| 4,910,402 A | | 3/1990 | McMillan |
| 5,146,413 A | * | 9/1992 | Shires ........................ 702/25 |
| 5,192,984 A | * | 3/1993 | Beecher et al. .............. 356/433 |
| 5,490,909 A | * | 2/1996 | Wang et al. ................. 204/452 |
| 5,557,398 A | | 9/1996 | Wechsler et al. |
| 5,672,873 A | * | 9/1997 | Yamazoe ............... 250/339.12 |
| 5,766,875 A | | 6/1998 | Hafeman et al. |
| 5,791,345 A | | 8/1998 | Ishihara et al. |
| 5,844,124 A | * | 12/1998 | Shimokawatoko et al. . 73/23.34 |
| 6,091,490 A | * | 7/2000 | Stellman et al. ............. 356/300 |
| 6,151,111 A | | 11/2000 | Wechsler et al. |
| 6,188,474 B1 | | 2/2001 | Dussault et al. |
| 6,195,574 B1 | | 2/2001 | Kumar et al. |
| 6,982,431 B2 | | 10/2002 | Modlin et al. |
| 6,475,339 B1 | * | 11/2002 | Chai et al. .................... 162/49 |
| 6,628,382 B2 | | 9/2003 | Robertson |
| 6,693,709 B2 | | 2/2004 | Wechsler et al. |
| 6,747,740 B1 | | 6/2004 | Leveille et al. |
| 6,794,649 B2 | * | 9/2004 | Thrash et al. .......... 250/339.13 |
| 6,825,044 B2 | * | 11/2004 | Zheng et al. ................. 436/164 |
| 6,825,921 B1 | | 11/2004 | Modlin et al. |
| 6,867,861 B2 | * | 3/2005 | Martino et al. .............. 356/319 |
| 7,316,898 B2 | * | 1/2008 | Sweeney ........................ 435/5 |
| 2005/0019936 A1 | | 1/2005 | Samsoonder et al. |
| 2006/0166238 A1 | * | 7/2006 | Ramsing et al. ................ 435/6 |
| 2009/0166520 A1 | * | 7/2009 | Tuli et al. .................... 250/253 |

OTHER PUBLICATIONS

Levine, SL and Sunners, B. Telescoping Sperctrophotometer Dip Probe, IBM Prior Art Database IPCOM000085523D.*

* cited by examiner

*Primary Examiner*—Gregory J Toatley
*Assistant Examiner*—Jarreas C Underwood
(74) *Attorney, Agent, or Firm*—G Kenneth Smith

(57) ABSTRACT

This disclosure relates generally to a sampling device, and, more particularly, a sampling device that facilitates spectroscopic measurements with a variable path length and the necessary software controlled algorithms, and methods for using such a device.

23 Claims, 16 Drawing Sheets

Variable Pathlength Device Software: Setup

Variable Pathlength Device Software: Data Acquisition Page-1

Variable Pathlength Device Software: Data Acquisition Page-2

Variable Pathlength Device Software: Kinetic Acquisition

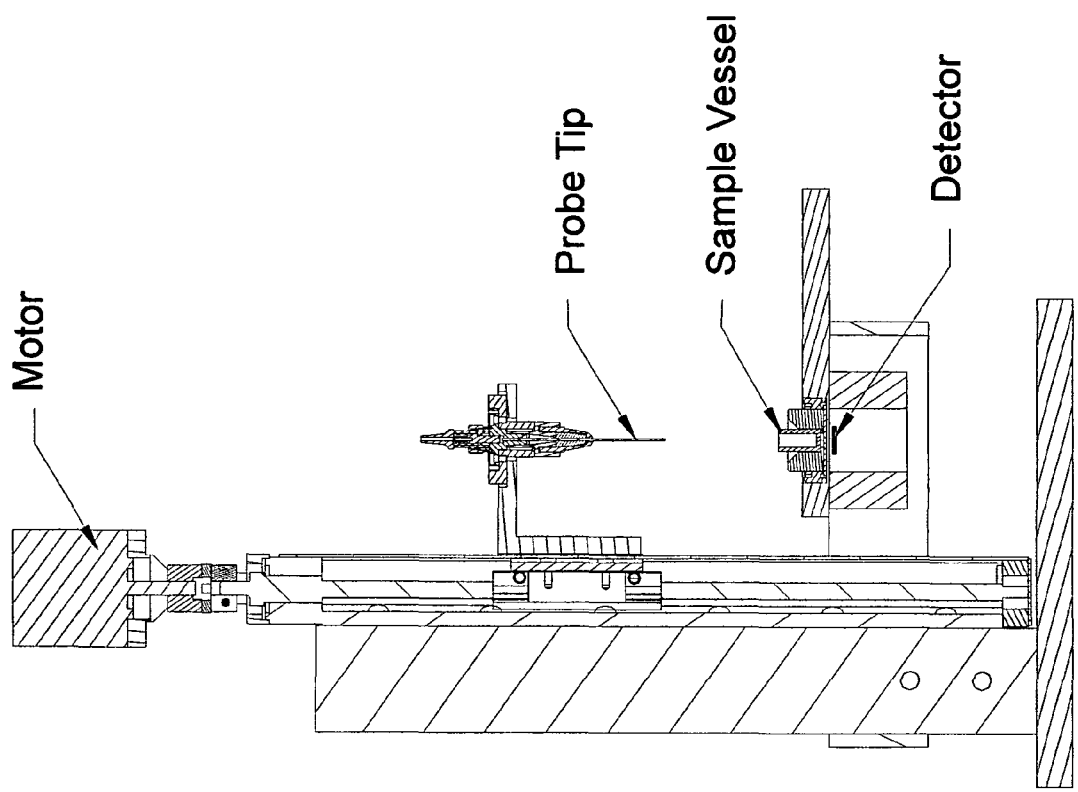

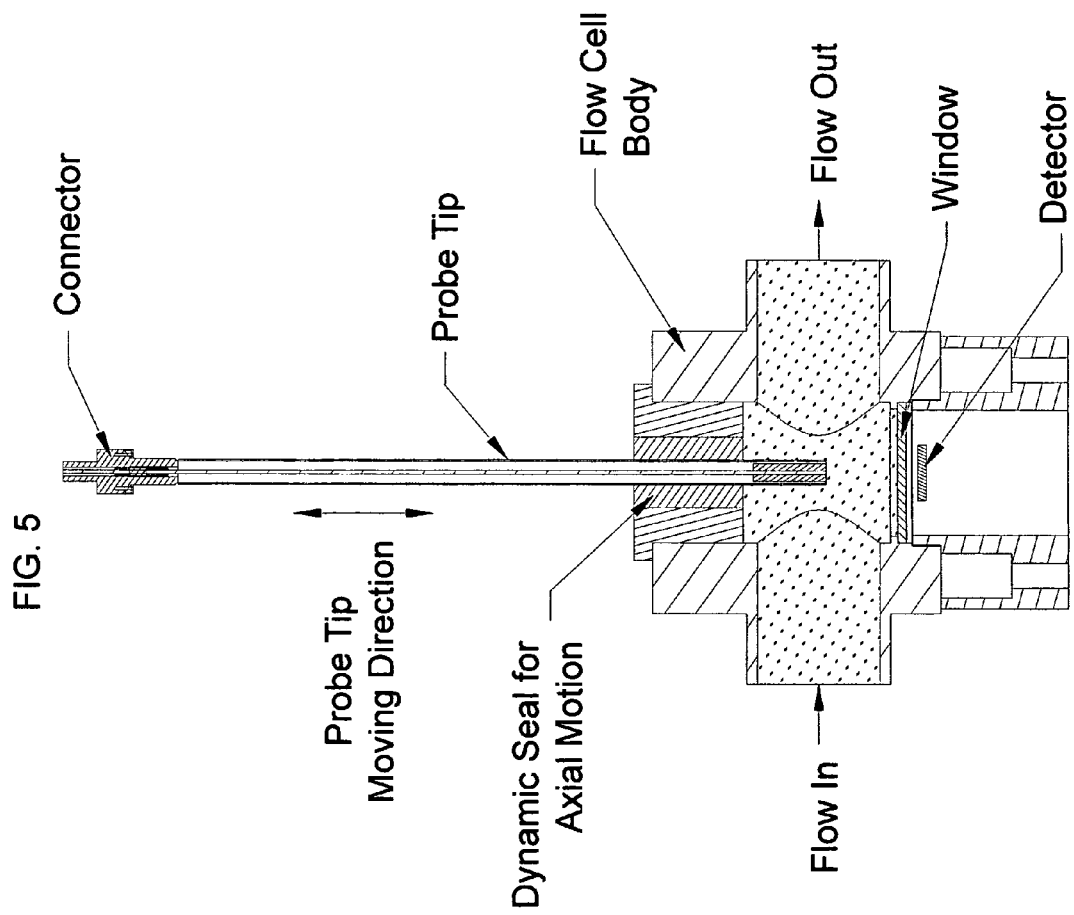

CSA Spectrum

INTERACTIVE VARIABLE PATHLENGTH DEVICE

This application claims benefit under 35 USC §119(e) of the U.S. Provisional patent Application Ser. No. 60/923,179 filed Apr. 13, 2007.

FIELD OF THE INVENTION

The present invention relates generally to a sampling device, and, more particularly, a sampling device that facilitates spectroscopic measurements with a variable path length and the necessary software controlled algorithms and methods for using such a device.

BACKGROUND OF THE INVENTION

Spectroscopic analysis is a broad field in which the composition and properties of a material in any phase, gas, liquid, solid, are determined from the electromagnetic spectra arising from the interaction (eg. absorption, luminescence, or emission) with energy. One aspect of spectrochemical analysis, known as spectroscopy, involves interaction of radiant energy with the material of interest. The particular methods used to study such matter-radiation interactions define many sub-fields of spectroscopy. One field in particular is known as absorption spectroscopy, in which the optical absorption spectra of liquid substances are measured. The absorption spectra is the distribution of light attenuation (due to absorbance) as a function of light wavelength. In a simple spectrophotometer the sample substance which is to be studied is placed in a transparent container, also known as a cuvette or sample cell. Electromagnetic radiation (light) of a known wavelength, $\lambda$, (ie. ultraviolet, infrared, visible, etc.) and intensity I is incident on one side of the cuvette. A detector, which measures the intensity of the exiting light, I is placed on the opposite side of the cuvette. The length that the light propagates through the sample is the distance d. Most standard UV/visible spectrophotometers utilize standard cuvettes which have 1 cm path lengths and normally hold 50 to 2000 μL of sample. For a sample consisting of a single homogeneous substance with a concentration c, the light transmitted through the sample will follow a relationship know as Beer's Law: $A=\epsilon cl$ where A is the absorbance (also known as the optical density (OD) of the sample at wavelength $\lambda$ where OD=the −log of the ratio of transmitted light to the incident light), $\epsilon$ is the absorptivity or extinction coefficient (normally at constant at a given wavelength), c is the concentration of the sample and l is the path length of light through the sample.

Spectroscopic measurements of solutions are widely used in various fields. Often the compound of interest in solution is highly concentrated. For example, certain biological samples, such as proteins, DNA or RNA are often isolated in concentrations that fall outside the linear range of the spectrophotometer when absorbance is measured. Therefore, dilution of the sample is often required to measure an absorbance value that falls within the linear range of the instrument. Frequently multiple dilutions of the sample are required which leads to both dilution errors and the removal of the sample diluted for any downstream application. It is, therefore, desirable to take existing samples with no knowledge of the possible concentration and measure the absorption of these samples without dilution.

Multiple sample cuvettes may solve the problem of repetitive sampling, however, this approach still requires the preparation of multiple sample cuvettes and removes some sample from further use. Furthermore, in most spectrophotometers the path length, l, is fixed.

Another approach to the dilution problem is to reduce the path length in making the absorbance measurement. By reducing the measurement path length, the sample volume can be reduced. Reduction of the path length also decreases the measured absorption proportionally to the path length decrease. For example, a reduction of path length from the standard 1 cm to a path length of 0.2 mm provides a virtual fifty-fold dilution. Therefore, the absorbance of more highly concentrated samples can be measure within the linear range of the instrument if the path length of the light travelling through the sample is decreased. There are several companies that manufacture cuvettes that while maintaining the 1 $cm^2$ dimension of standard cuvettes decrease the path length through the sample by decreasing the interior volume. By decreasing the interior volume less sample is required and a more concentrated sample can be measured within the linear range of most standard spectrophotometers. While these low volume cuvettes enable the measurement of more concentrated samples the path length within these cuvettes is still fixed. If the sample concentration falls outside the linear range of the spectrophotometer the sample still may need to be diluted or another cuvette with an even smaller path length may be required before an accurate absorbance reading can be made.

The prior art also describes spectrophotometers and flow cells that are capable of measuring absorbance values of low volume samples. These devices are designed to utilize short path lengths for measuring absorbance so that only small amounts of sample are required. U.S. Pat. No. 4,643,580 to Gross et al. discloses a photometer head in which there is a housing for receiving and supporting small test volumes. A fiber optic transmitter and receiver are spaced within the housing so that a drop can be suspended between two ends.

U.S. Pat. No. 4,910,402 to McMillan discloses an apparatus in which a syringe drops liquid into the gap between two fixed fibers and an IR pulse from an LED laser is fed through the droplet. The output signal is analyzed as a function of the interaction of the radiation with the liquid of the drop.

U.S. Pat. No. 6,628,382 to Robertson describes an apparatus for performing spectrophotometric measurements on extremely small liquid samples in which a drop is held between two opposing surfaces by surface tension. The two surfaces can move relative to one another to keep the surface tension in a sample such that a spectrophotometric measurement by optical fibers can be made.

U.S. Pat. No. 6,747,740 to Leveille et al. describes a photometric measurement flow cell having measurement path lengths that can be adjusted down to less than 0.1 mm. The flow cell contains a stepped optical element which includes a stem portion that can be made to various lengths. The measurement path length can be adjusted by replacing one of the stepped elements of a particular length with another stepped element or a different length.

U.S. Pat. No. 6,188,474 to Dussault et al. describes a sample cell for use in spectroscopy that included two adjustable plates that enable a user to vary the cross sectional geometry of a sample cell flow path between two or more configurations.

U.S. Pat. No. 6,091,490 to Stellman et al. describes a fiber optic pipette coupled to a glass capillary for spectrophotometric measurements of small volume samples utilizing long path length capillary spectroscopy.

There are a series of patents assigned to Molecular Devices Corporation including U.S. Pat. No. 6,982,431 that describe a microplate reader capable of determining absorption measurements for multiple liquid samples in microtiter plates. Each well of the microtiter plate may provide for a different light path length based on the amount of sample solution in each well and the curvature of the meniscus of the solution in each well.

While some of these instruments provide the capability of varying the path length for measurement of highly concentrated low volume samples the applications described therein relate primarily to single path length and single wavelength measurements. Several of the instruments provide a limited number of path lengths and all are limited to path length larger than 0.2 mm. Furthermore, the devices and methods of the prior art do not provide for expanding the dynamic range of the spectrophotometer so that it is not necessary to adjust the concentration of the sample to fall within the linear range of absorbance detection of the instrument. To the extent that the prior art teaches shorter path lengths to determine the concentration of very concentrated samples or low volume samples the focus of these devices is to take a single absorbance reading at a single path length. As such the prior art references require that the path length be known with great accuracy so that an accurate concentration measurement can be made.

The present invention provides devices and methods that provide a variable path length spectrophotometer which dynamically adapts parameters in response to real time measurements via software control to expand the dynamic range of a conventionally spectrophotometer such that samples of almost any concentration can be measured without dilution or concentration of the original sample. Furthermore, certain methods of the present invention do not require that the path length be known to determine the concentration of samples. This and other objects and advantages of the invention, as well as additional inventive features, will be apparent from the description of the invention provided herein.

SUMMARY OF THE INVENTION

The present invention overcomes the disadvantages and shortcomings of the prior art by providing an interactive variable path length devices and methods for spectroscopic measurement of a sample. The instruments of the present invention can be used to measure the concentration of very concentrated samples by providing path lengths around 0.2 μm and above. Such small path lengths permit the measurement of samples too concentrated to be measured by conventional spectrophotometers. Furthermore, the instruments and methods of the present invention can provide spectrum scans in two or three different path length zones. This enables users to determine optimal absorbance peaks in a sample in a single run. The benefit of this method is that it can provide information on optimization of concentration measurements by comparing absorbance peak data at multiple path lengths and multiple wavelengths as these values can be different due to the contents in the sample. Instruments that use standard fixed path length cuvettes can not present all of this data at the same time. The variable path length instrument may include a probe tip, sample vessel, a mechanism for moving the probe tip and sample vessel relative to one another (eg. the sample vessel is stationary and the probe moves or the probe is stationary and the sample vessel moves or both are capable of movement), delivery optical fiber, detector and appropriate software for path length control and measurement parameters.

The present invention includes methods of determining the concentration of a sample comprising placing the sample in a vessel; moving a probe relative to the vessel such that the probe makes contact with the bottom of the vessel; moving the probe relative to the vessel such that the probe moves from the bottom of the vessel through the sample by a predetermined increment such that a preselected path length through the solution is obtained; taking an absorbance reading at a predetermined wavelength; repeating steps of moving the probe relative to the sample and taking a measurement; generating a regression line from the absorbance and path length such that a slope of the regression line is obtained; determining the concentration of the sample by dividing the slope of the regression line by the extinction coefficient of the sample.

The present invention also includes instruments for determining the concentration of a sample at multiple path lengths comprising a light source operably linked to a probe; a sample vessel that can contain the sample; a motor operably linked to the sample vessel such that the sample vessel can be moved relative to the probe to provide variable path lengths; a probe that can carry electromagnetic radiation that can be moved relative to the sample vessel by the motor, a detector that can detect electromagnetic radiation disposed such that the detector is substantially perpendicular to the electromagnetic radiation emanating from the probe; and software that can calculate the concentration of the sample based on the information provided by the detector at the predetermined path length.

The instruments and methods of the present invention can be used in conjunction with a standard spectrophotometer which may be used to provide an electromagnetic source and/or a detector for measuring electromagnetic radiation.

FIGURES

FIG. 4A is a schematic of one embodiment of the instrument of the present invention.

FIG. 5 is a schematic of a flow-through device which may serve as a sample vessel in the instruments of the present invention.

Figure 13:
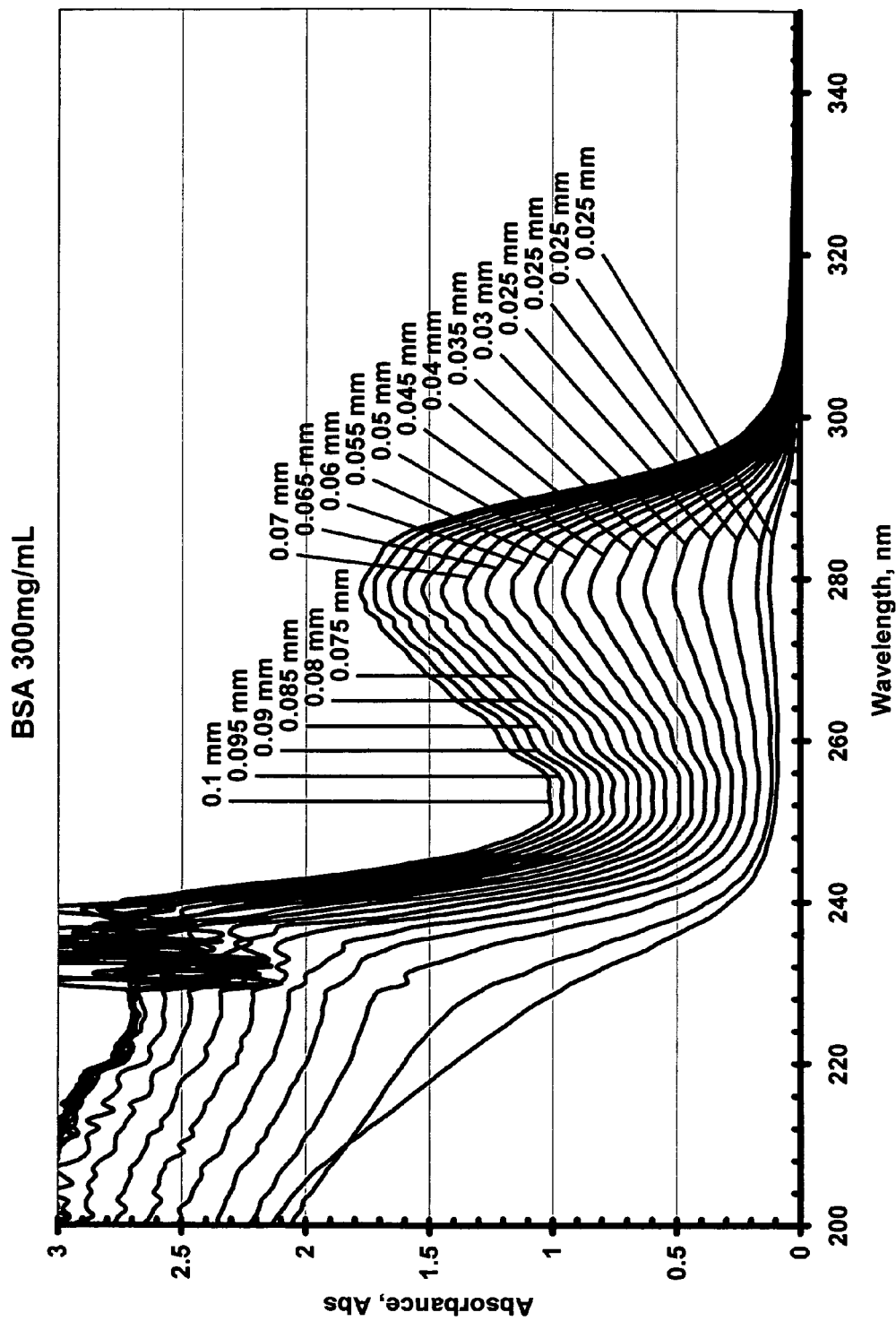
Figure 14:
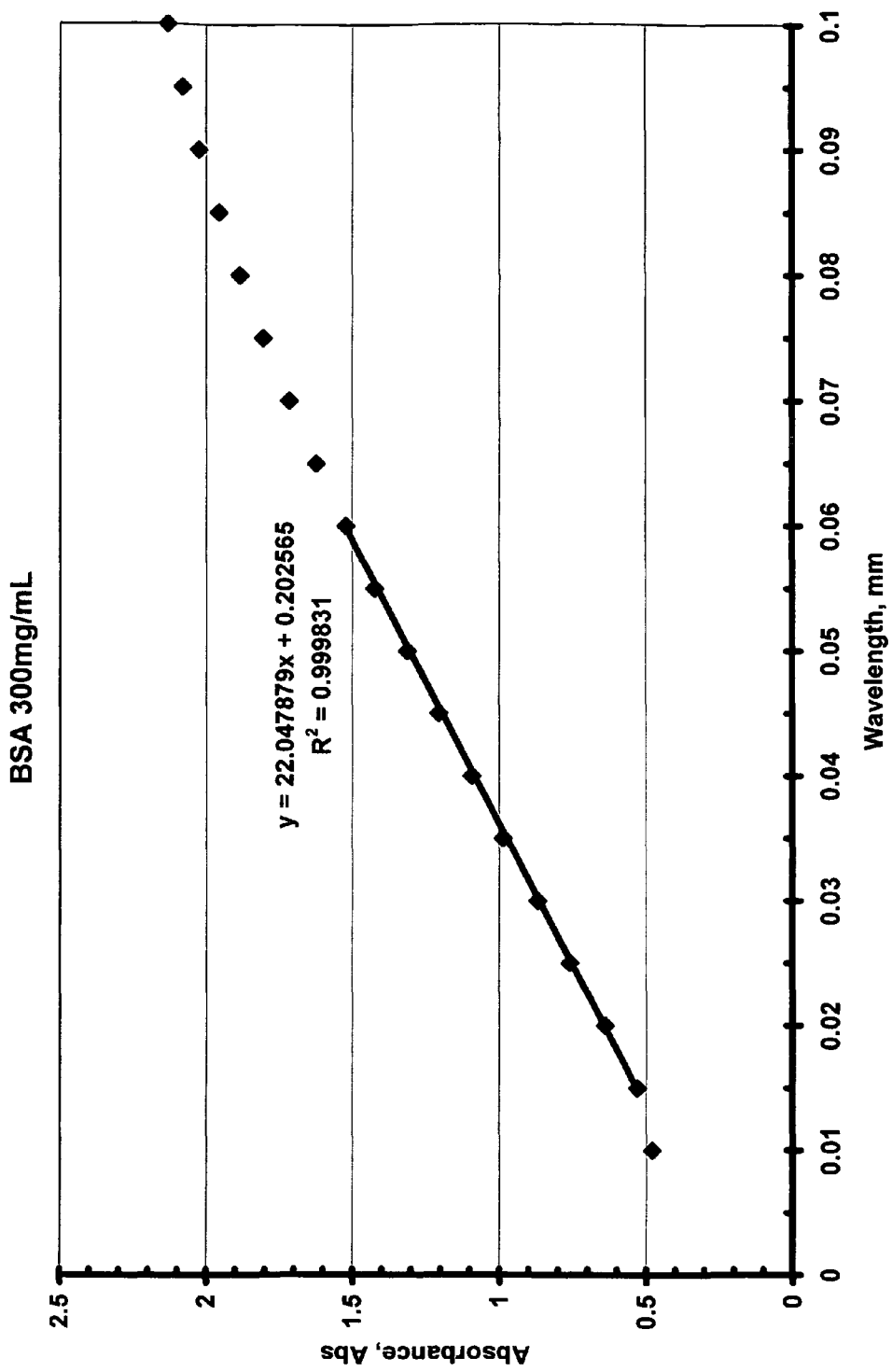

FIG. 13 is the spectra of BSA from 200 to 340 nm at multiple path lengths between 0.01 mm and 0.1 mm on an instrument of the present invention FIG. 14 is a plot of a linear regression line for the plot of the absorbance versus path length for BSA at 280 nm.

DEFINITIONS

The term "moving the probe relative to the vessel" or "moving the probe relative to the sample" means that the vessel or the sample relative to the probe is moved. This encompasses the situations where the probe is moving and the vessel or sample is stationary, the vessel or sample is moving and the probe is stationary and where the sample or the vessel is moving and the probe is moving.

The term "taking an absorbance reading" means that any absorbance reading(s) is measured by the device or instrument. This encompasses situations where the absorbance reading is taken at a single wavelength and/or a single path length or where the reading is taken at multiple wavelengths (such as in a scan) and/or multiple path lengths.

The term "sample(s)" may include, but is not limited to, compounds, mixtures, surfaces, solutions, emulsions, suspensions, cell cultures, fermentation cultures, cells, tissues, secretions, and extracts.

The term "motor" is any device that can be controlled to provide a variable path length through a sample.

DETAILED DESCRIPTION OF THE INVENTION

The present invention relates to devices and methods for determining the spectrophotometric characteristics of a solution by employing an approach that permits the use of a variable path length for multiple determinations of the parameters of interest. For example, in determining the concentration of a compound in solution the present invention provides methods and devices for determining the absorbance of the solution at various path lengths. The values of the absorbance at various path lengths can then be used to calculate the concentration of the compound in the solution. The devices and methods of the present invention are particularly useful for determining the concentration of highly concentrated samples without resorting to single or multiple dilutions of the samples. This attribute is possible due to the small path lengths which the devices of the present invention can achieve. The instruments of the present invention can be used to measure the concentration of very concentrated samples by providing path lengths around 0.2 µm and longer. Preferably the instruments of the present invention can provide path lengths from about 0.5 µm and to about 15 cm and more preferably between about 1 µm to about 50 mm. The devices and methods also provide for measurement of concentrations of extremely dilute solutions by providing larger path lengths. In essence the devices and methods of the present invention expand the dynamic range of a standard spectrophotometer by permitting a wide range of path lengths for measuring the absorbance values of a solution. This broad dynamic range enables users to determine the concentrations of their samples without altering (diluting or concentrating) the samples. While preferred embodiments of the methods and devices of the present invention are for determining the absorbance, extinction coefficient or concentration of a particular sample or set of samples the devices and methods of the present invention may also be used in different modes such as scattering, luminescence, photoluminescence, photoluminescence polarization, time-resolved photoluminescence, photoluminescence life-times and chemiluminescence as well as other modalities. The devices and the methods of the present invention may be used to determine optical values of one or more samples at a given time. The invention contemplate the use of single sample formats such as cuvettes or any sample holder, as well as multiple sample formats such as microtiter plates and multiple cuvette or multiple sample arrangements.

The variable path length device of the present invention may be comprised of a probe tip, sample vessel, motor, delivery optical fiber, detector, unidirectional sliding mechanism and appropriate software for path length control and measurement parameters.

Probe Tip

In the present invention the probe tip is a light delivery device which delivers light to the sample. The probe tip may be a single light delivery device such as a fiber optic cable that interfaces with one or more electromagnetic sources to permit passage of light through the sample. Alternatively the probe tip may be housed in a probe tip assembly which may be comprised of a light delivery device, housing, end terminations and other optical components and coatings. The light delivery device can be fused silica, glass, plastic or any transmissible material appropriate for the wavelength range of the electromagnetic source and detector. The light delivery device may be comprised of a single fiber or of multiple fibers and these fibers can be of different diameters depending on the utilization of the instrument. The fibers can be of almost any diameter but in most embodiments the fiber diameter is in the range of from about 0.005 mm to about 20.0 mm. In a preferred embodiment the light delivery device is a single optical fiber with a diameter of from about 0.1 mm to about 1.0 mm. The probe tip optionally utilizes a housing to contain the light delivery device. This housing is used primarily to shield the light delivery device and may be made from metal, plastic, ceramic or any other material that is compatible with its usage. The probe tip may optionally include end terminations such as connectors, ferrules or anything that will facilitate a mechanical interconnection. The terminations can be polished, cleaved, shaped or manipulated in any fashion compatible with the device's usage. The instruments of the present invention include probe tips with additional optical components such as lenses or filters. The probe tips may include coatings on the end of the fiber tip to serve as filters, pH indicators, catalysts or as sealing mechanisms. The probe tip may be a permanent part of the instrument and/or probe assembly device or alternatively the probe tip may be detachable, such that it may be removed from the probe tip assembly. As a permanent part of the instrument the probe tip is an integral part of the light delivery device. In a preferred embodiment the probe tip is a single optical fiber which is attached at one end to the light source and at the other end immersed in the sample. Alternatively the probe tip may be detachable and in such embodiments the probe tip can be separated from the light delivery device though a variety of mechanisms. In a preferred embodiment the probe tip is attached to the light delivery device though a Touhey Borst adapter such that after usage the probe tip can be removed and replaced with another probe tip. The detachable probe tip is of a length sufficient to penetrate the sample and attach to the light delivery assembly. In preferred embodiments of the detachable probe tip the length of the probe tip is at least about 20 mm in length. Depending on its usage the probe tip may simply be thrown away after removal. Disposable probe tips obviate problems associated with cleaning the probe tip and avoid the potential of contamination from one sample to another. Instruments of the present invention include multiple probe tips that can be associated with a single light delivery device. Alternatively multiple light delivery devices may be associated with each probe tip.

The path length is the distance between the end of the probe tip and inside surface of the sample vessel holding the liquid, the inside surface being the surface of the vessel which is substantially perpendicular to the probe tip. The end surface of the probe tip, which both defines the path length and is in contact with the liquid, is substantially parallel to the inside surface of the sample vessel which is adjacent to the detector. In one embodiment, the probe tip is positioned above the sample vessel holding the sample and aligned so that the light exiting the probe tip will pass through the sample vessel onto a detector (or detection light guide). The probe tip is able to transmit wavelengths within the range of the instrument.

Light Source

The electromagnetic radiation source provides light in a predetermined fashion across a wide spectral range or in a narrow band. The light source may include arc lamps, incandescent lamps, fluorescent lamps, electroluminescent devices, laser, laser diodes, and light emitting diodes, as well as other sources. In a preferred embodiment the source of radiation is a Xenon arc lamp or tungsten lamp. In a preferred embodiment of the present invention the light source is coupled to the probe tip through a light guide. Alternatively the light source could be a light emitting diode that can be mounted directly onto the probe tip.

Sample Vessel

The vessel must be able to contain the liquid and allow light to pass through it onto the detection light guide or detector. The vessel will also have an opening to allow the probe tip to delivering light, to penetrate the liquid. This vessel should be able to transmit wavelengths within the range of the instrument typically from about 200-1100 nm. For ultraviolet application a quartz vessel may be required, but often plastic vessels will made of cyclo olefin polymer (COP), cyclo olefin copolymer (COC), polystyrene (PS) or polymethyl methacrylate (PMMA) will suffice. The sample vessels used with the present invention can be of different sizes and shapes depending upon the application and the amount of sample available for analysis. The sample vessels of the present invention may be anything that permits an absorbance value to be taken. Such vessels include stationary sample vessels as a cuvette or microtiter plate or moving samples as in a flow-through device (FIG. 5). The sample size may be between 0.1 µL to several liters in a stationary sample. The preferred shape of the vessel is one with the side facing the detector being substantially flat and substantially parallel to the face of the detector. The detector may be situated at a slight angle to the vessel to reduce noise due to back reflection of the electromagnetic radiation coming through the sample. The sample vessel may have multiple wells such as in a microtiter plate. The sample vessel may be coated with optical materials or chemicals or biochemicals such as antibodies. The sample vessel may optionally be heated or cooled by the instrument and may be held in a sealed area that can be sterile or non-sterile. The sample may be held in a sample holder supported by a stage. The sample can include compounds, mixtures, surfaces, solutions, emulsions, suspensions, cell cultures, fermentation cultures, cells, tissues, secretions, extracts, etc. Analysis of the sample may involve measuring the presence, concentration or physical properties of a photoactive analyte in such a composition. Samples may refer to contents of a single well or cuvette or sample holder or may refer to multiple samples within a microtiter plate. In some embodiments the stage may be outside the instrument.

Motor

The motor drives the tip probe into and out of the vessel. The motor drives the probe tip in precise steps to vary the path length through the sample. Path length changes can be from zero mm and larger depending upon device configuration. The motor permits the movement of the probe within the sample to place the probe tip at the precise pre-determined path length. Motors that can be used with the instruments of the present invention include stepper motors, servo, piezo, electric and magnetic motors or any device that can be controlled to provide a variable path length through a sample. In a preferred embodiment of the instruments of the present invention the motor drives a stage on which the sample vessel rests so that the probe tip moves relative to the sample vessel. In this configuration the stage and the probe move relative to each other in increments which range from 0.2 µm to 1 cm. In a preferred embodiment the range of increment is between from about 1 µm to about 50 µm. The relative motion of the stage to the probe is accurate to with a resolution of 0.2 µm or less. In a preferred embodiment of the instruments of the invention the resolution of the relative motion of the probe and the stage is between about 0.5 µm to about 0.01 µm.

Unidirectional Sliding Mechanism

The unidirectional sliding mechanism is a system designed to permit physical contact between the end of the probe tip and the "bottom" (perpendicular to the probe tip) of the sample vessel in order to establish a "zero path length" position which is an approximate zero benchmark from which all other path lengths can be referenced. In a preferred embodiment of the present invention the unidirectional sliding mechanism insures that the probe tip makes physical contact with the sample vessel surface thereby guaranteeing that the probe tip is in the "zero path length" position. Physical contact should to be achieved without causing damage to either the sample vessel or the probe tip. In a preferred embodiment the position is achieved by allowing/requiring linear displacement of either the sample vessel of the probe tip in one direction once the physical contact is achieved. This allows displacement in the direction that zero path length position is set, much in the same way as using the tare feature on a scale. The motion is constrained to reduce or eliminate backlash or recoil as the probe tip and vessel surface are separated. The device capable of these features is referred to as a unidirectional sliding mechanism. There are numerous embodiments of the unidirectional sliding mechanism.

In a preferred embodiment, the unidirectional sliding mechanism comprises a modeled plastic coupling device called a Touhy Borst Adapter (TBA) which contains a silicone rubber or similarly compliant gasket material with a hole in the center of it which is housed by two threaded plastic components which when screwed together compress the internal gasket, thus reducing the diameter of the internal hole creating a seal around anything within the hole. The amount of sealing and compression can be controlled by the changing the length of threaded engagement between the two threaded components of the TBA. In a preferred embodiment, the probe tip is inserting through the hole in the TBA gasket and then the TBA is tightened to compress the TBA gasket around the probe tip. The threading is adjusted so the frictional force between the probe tip and the TBA gasket exceeds the weight of the probe tip, thus not allowing the probe tip to fall out of the TBA when held vertically, but not so tight that the probe tip is unable to slide inside of the gasket. This frictional interaction results in a unidirectional sliding displacement that allows the establishment of the zero path length position.

There are other means and mechanisms by which this can be achieved. In one embodiment a thin membrane with a hole, a linear slit or two orthogonal slits enclosed between two blocks contains a hole slightly larger than the probe tip such that the probe tip can be inserted into the blocks and the membrane creates the frictional force that allows displacement in one direction.

In another embodiment the coupling mechanism for the probe tip or the sample vessel can comprise a spring loaded tapered sliding coupling that releases the probe tip or sample vessel when a force is applied in one direction, but grips more tightly when the force is released, similar to a spring loaded compression ring.

In another embodiment the coupling mechanism for the probe tip of the sample vessel can comprise a spring loaded ratchet mechanism which displaces a toothed slide which locks in place when displaced in one direction, but would require a release button to allow unloading or motion in the opposite direction.

In each of the embodiments of the unidirectional sliding mechanism the zero path length position is set passively, meaning the user does not need to interact with the device other than driving the motion of the system to achieve the physical contact condition. There are other embodiments that require intervention of the user, which may be utilized for long path length and flow versions of the instruments of the present invention. In one embodiment, the probe tip coupling mechanism has a sliding coupling. After physical contact is achieved and displacement has occurred the user will set the displacement by means of a thumb screw, a set screw, tightening a collect, mechanical clamp, magnetic clamp or other means of locking the position of either the probe tip, probe tip coupling mechanism, the sample vessel or the sample vessel holding device.

Detector

Detectors comprise any mechanism capable of converting energy from detected light into signals that may be processed by the device. Suitable detectors include photomultiplier tubes, photodiodes, avalanche photodiodes, charge-coupled devices (CCD), and intensified CCDs, among others. Depending on the detector, light source, and assay mode such detectors may be used in a variety of detection modes including but not limited to discrete, analog, point or imaging modes. Detectors can used to measure absorbance, photoluminescence and scattering. The devices of the present invention may use one or more detectors although in a preferred embodiment a single detector is used. In a preferred embodiment a photomultiplier tube is used as the detector. The detectors of the instrument of the present invention can either be integrated to the instrument of can be located remotely by operably linking the detector to a light delivery device that can carry the electromagnetic radiation the travels through the sample to the detector. The light delivery device can be fused silica, glass, plastic or any transmissible material appropriate for the wavelength range of the electromagnetic source and detector. The light delivery device may be comprised of a single fiber or of multiple fibers and these fibers can be of different diameters depending on the utilization of the instrument. The fibers can be of almost any diameter but in most embodiments the fiber diameter is in the range of from about 0.005 mm to about 20.0 mm.

One preferred embodiment of the instruments of the present invention has the optics of the system oriented such that the probe tip is on "top" and the detector is on the "bottom" (FIG. 4). In this vertical orientation the sample vessel is above the detector and the probe tip can move up and down, into and out of the sample vessel such that the light form the probe tip moves through the sample within the sample vessel and impinges on the detector below. Other orientations are possible such as in a flow-cell system where the detector and probe tip may be in a substantially horizontal orientation (FIG. 5) and the sample flows between the detector and the probe. Regardless of the absolute spatial orientation or the probe and detector, the probe tip and surface of the detector should be substantially perpendicular relative to one another.

Software

Figure 1:
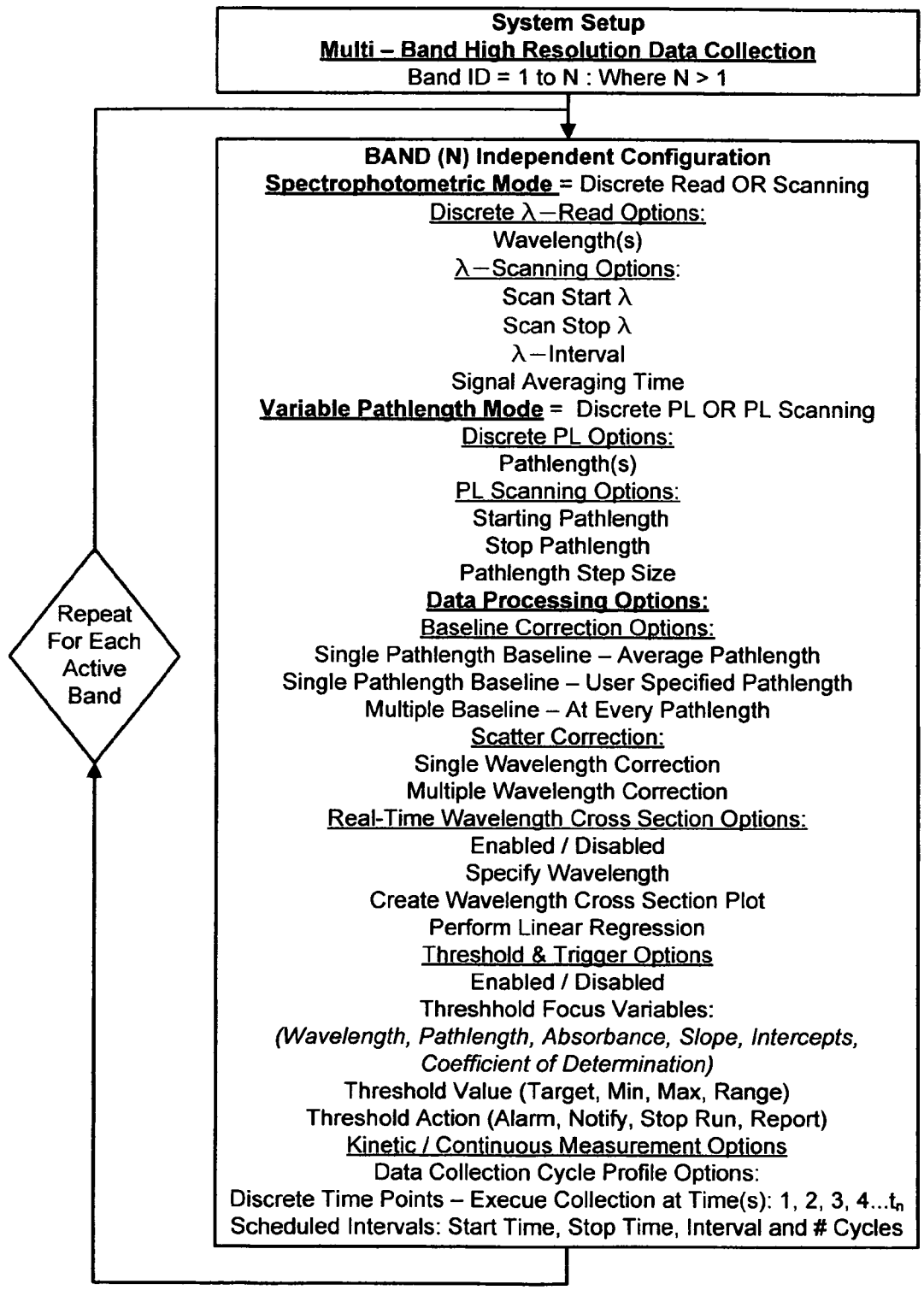
FIG. 1 is a flow diagram of one possible embodiment of the variable path length device software set up.
Figure 2:
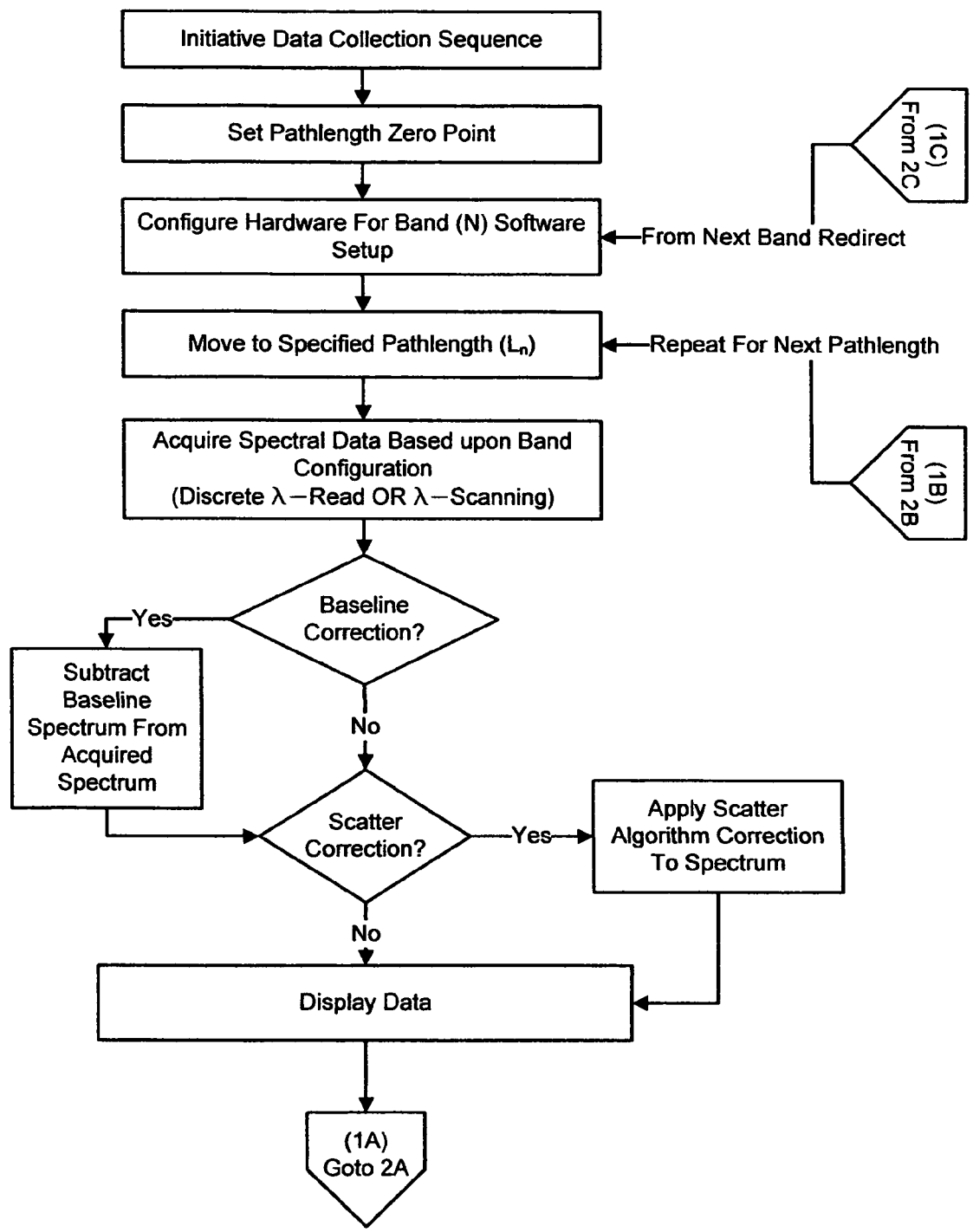
FIGS. 2A and 2B are flow diagrams of the data acquisition of the variable path length instrument software.
Figure 2:
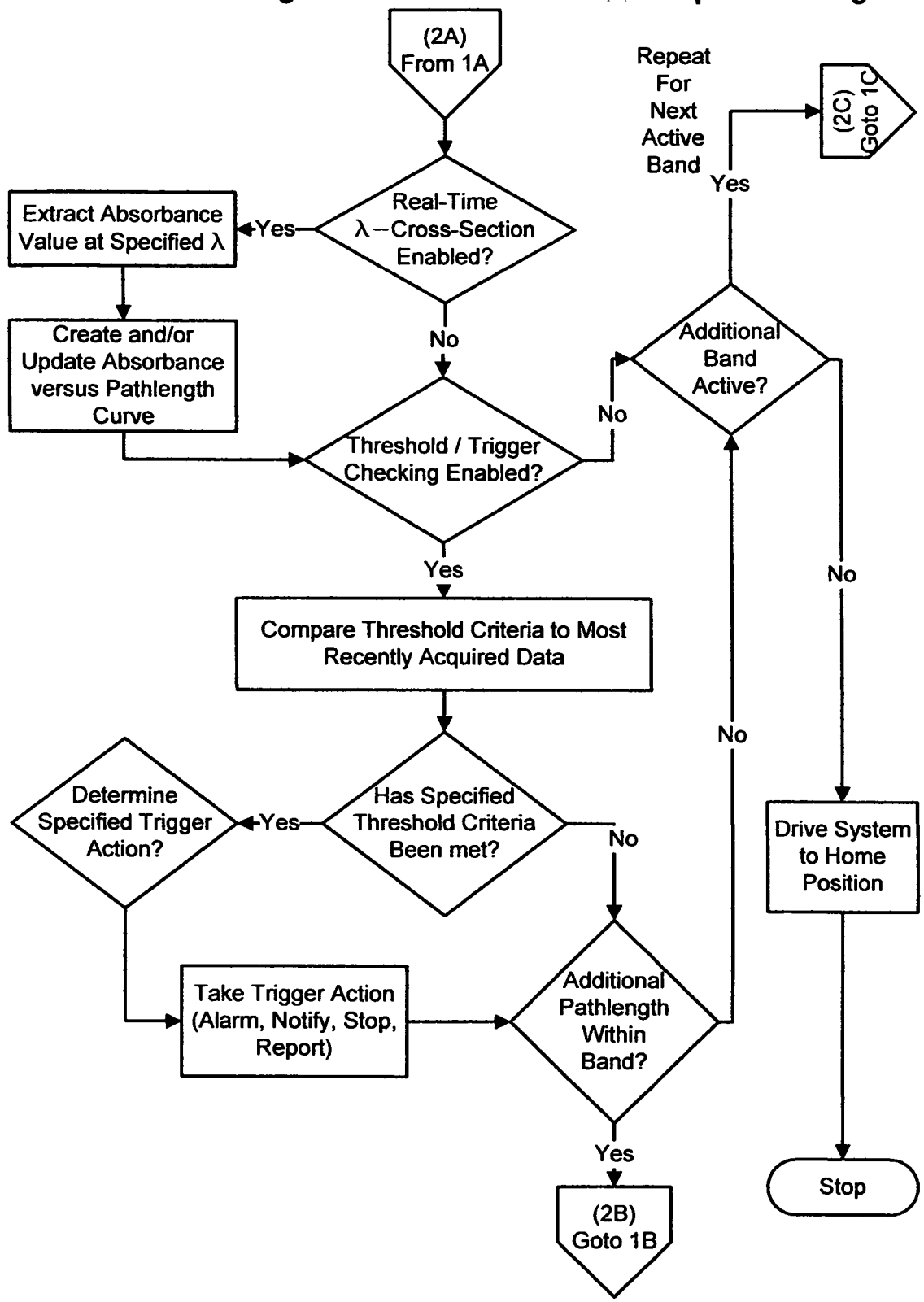
Figure 3:
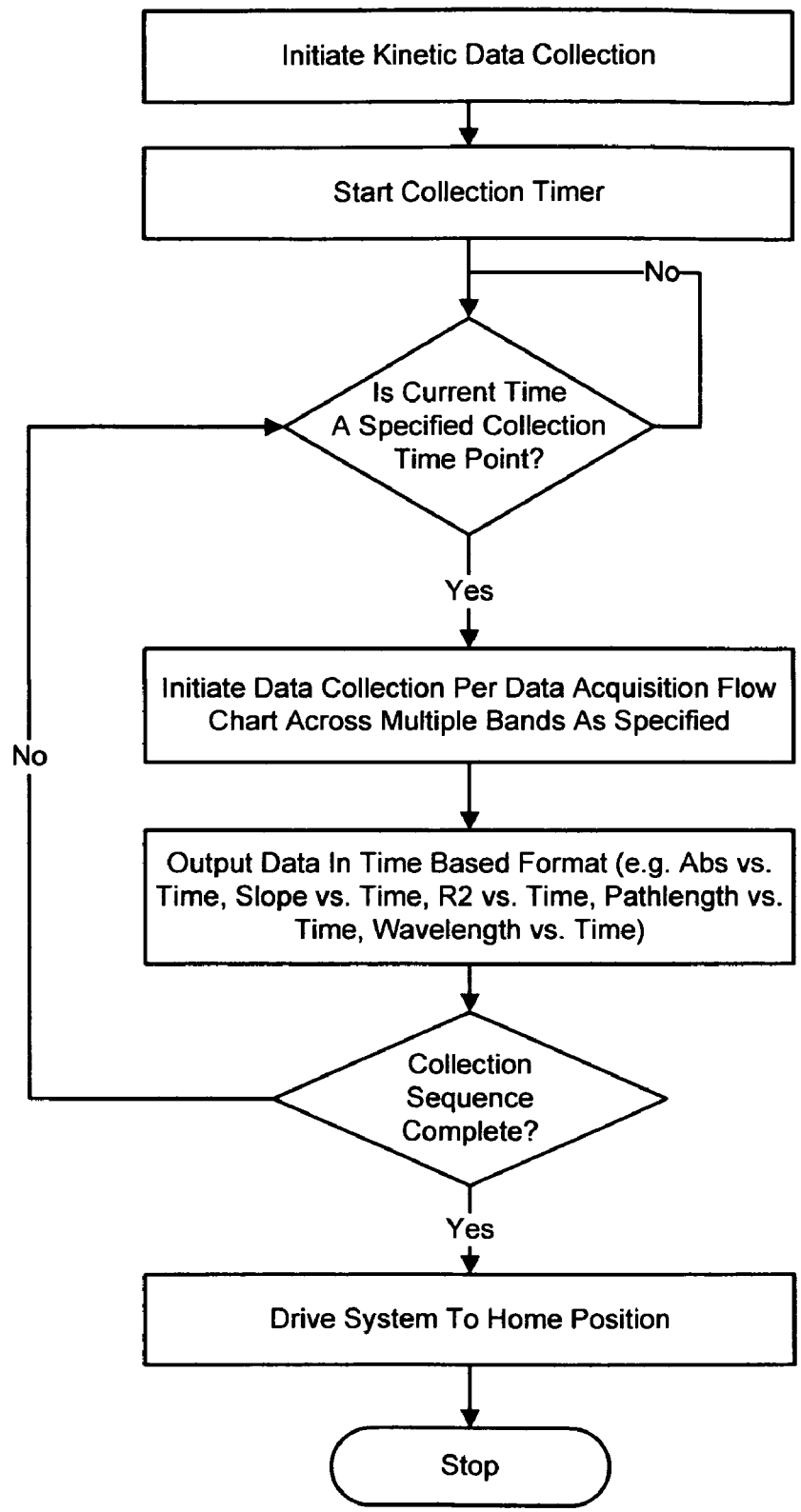
FIG. 3 is a flow diagram of the data acquisition of the variable path length instrument software
Figure 4B:
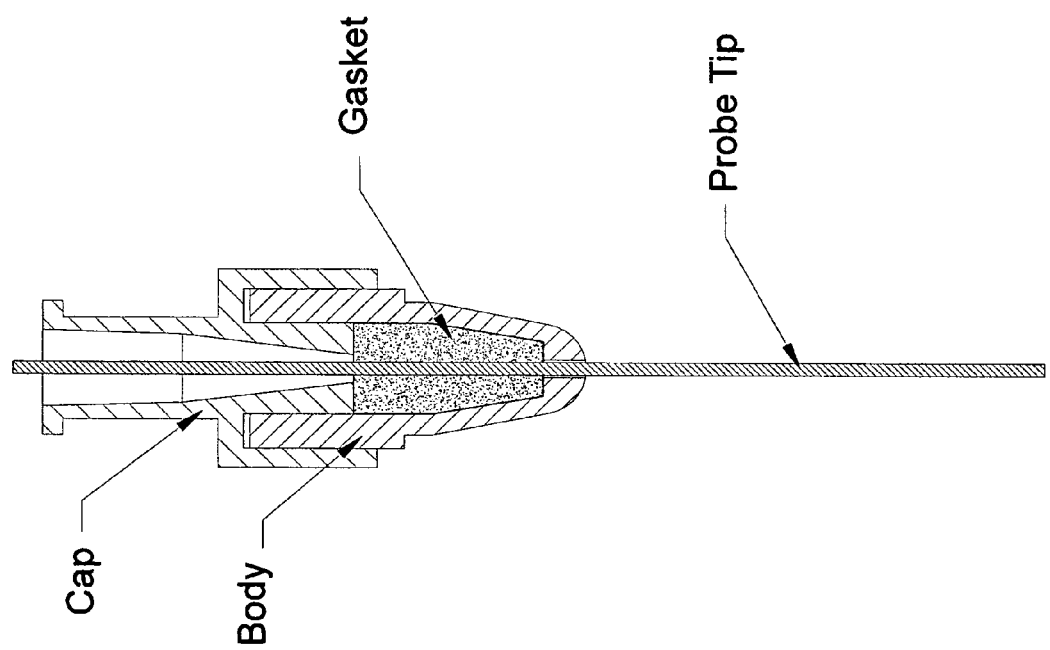
FIG. 4B is a schematic of one embodiment of the probe tip assembly.

The control software will adapt the devices behavior based upon various criteria such as but not limited to wavelength, path length, data acquisition modes (for both wavelength/path length), kinetics, triggers/targets, discrete path length/wavelength bands to provide different dynamic ranges/resolutions for different areas of the spectrum, cross sectional plot to create abs/path length curves, regression algorithms and slope determination, concentration determination from slope values, extinction coefficient determination, base line correction, and scatter correction. FIG. 1 is a flow diagram of an embodiment of the software scheme of the present invention. The software is configured to provide scanning or discrete wavelength read options, signal averaging times, wavelength interval, scanning or discrete path length read options, data processing option such as base line correction, scatter correction, real-time wavelength cross-section, threshold options (such as wavelength, path length, absorbance, slope, intercept, coefficient of determination, etc.) an kinetic/continuous measurement options. FIGS. 2A and 2B are flow diagrams of one embodiment of the data acquisition of the variable path length instrument software. FIG. 3 is a flow diagram of one embodiment of the data acquisition of real-time data collection that can be integrated into the data acquisition program. FIG. 4A is a schematic of one embodiment of the instruments of the present invention. The motor (1) drives the stage (4) on which the sample vessel (3) sits. The fiber tip probe (2) is fixed with respect to the motor such that as the stage moves up and down the probe distance to the sample vessel is increase or decreased respectively. Beneath the stage is the detector (5) which receives electromagnetic radiation from the probe tip once it has passed through the sample. FIG. 4B is a schematic of one embodiment of the probe tip assembly.

FIG. 5 is a schematic of a flow-through device which may serve as a sample vessel in the instruments of the present invention. The flow-through device comprises a flow cell body (8) that permits the flow of a sample solution into and out of the flow cell device. The flow cell body (8) has at least one window (7) that is transparent to electromagnetic radiation in the range of electromagnetic source typically 200-1100 nm. The window can be made from various materials but for ultraviolet applications quartz, cyclo olefin polymer (COP), cyclo olefin copolymer (COC), polystyrene (PS) or polymethyl methacrylate PMMA may be required. The window may be of different sizes and shapes so long as the electromagnetic radiation can pass through the window and strike the detector (5). The flow cell body also comprises a port through which the probe tip may pass. This port is sealed with a dynamic seal (9) such that the probe tip can pass through the port without sample solution leaking from the flow-through device. Such seals include FlexiSeal Rod and Piston Seals available from Parker Hannifin Corporation EPS Division, West Salt Lake City, Utah. In the diagram there is a single pathway for the sample solution to flow coming in the inlet port and exiting the outlet port. Alternative embodiments may include multiple pathways and multiple inlet and outlet ports. In the embodiment of the flow cell device in FIG. 5, the probe tip moves substantially perpendicular to the flow of the sample solution and is substantially perpendicular to the detector.

In one embodiment of the methods of the present invention multiple absorbance measurements may be taken at multiple path lengths without accurately knowing what the path length distance is. The prior art is replete with methods teaching how to accurately determine the path length in an absorbance reading so that an accurate determination of the concentration of the sample can be made including, for example, U.S. Pat. No. 6,496,260. In this embodiment of the present invention multiple absorbance measurements made at different path lengths enables an accurate calculation of the concentration based upon the instrument's ability to calculate a regression line from the absorbance and path length information. The slope of the regression line can then be used to calculate the concentration of the sample. Each path length need not be accurately known due to the fact that the software used to calculate the regression line can be programmed to select the most accurate line from the data set presented. The number of data points taken in these methods tends to "smooth out" any perturbations in the path length or absorbance reading such that regression lines with very high $R^2$ values can be obtained. In the methods of the present invention $R^2$ values of at least 0.99999 have been achieved. Obviously the higher the $R^2$ value the more accurate the slope which results in a highly accurate determination of the concentration of the sample. Any $R^2$ value between 0 and 0.99999 is achievable in the instruments and methods of the present invention, however in preferred embodiments of the methods of the present invention the $R^2$ value exceeds 0.95000 and in more preferred embodiments the $R^2$ will exceed 0.99500. In a preferred embodiment of the present invention the $R^2$ value is between about 0.95000 and about 0.99999. Other preferred embodiments include $R^2$ values between about 0.99500 and about 0.99999 and about 0.99990 and about 0.99999. While $R^2$ is a preferred measure of goodness-of-fit for the linear regression any other mathematic expression that measures goodness-of-fit can be utilized in the methods of the present invention.

The instruments and methods of the present invention allow the user to optimize the collection of data by selecting a pre-determined parameter such as absorbance. The user can define, for example, an absorbance of 1.0 and have the instrument search for other parameters (such as wavelength or path length) at which the absorbance of the sample is 1.0. This feature enables the user to define the parameters for the experiment without having to make multiple dilutions or constantly change the parameters of the instrument manually. The software of the present invention also permits the user to define an expected $R^2$ value so that the level of accuracy for the outcome can be defined prior to the data acquisition.

The instruments and methods of the present invention permit the collection of a variety of data sets including three dimension data sets that include measurement of absorbance, path length and wavelength. The software enables the user to generate three dimensional graphs of these data sets. Furthermore, the instruments and methods or the present invention provide for the collection of real-time data.

The instruments and methods of the present invention enable the calculation of the extinction coefficient of a particular sample at different wavelengths. The extinction coefficient, also known as absorptivity, is the absorbance of a solution per unit path length and concentration at a given wavelength. If the extinction coefficient for a given sample is known at a first wavelength ($\epsilon_1$) one can calculate the extinction coefficient at a second wavelength ($\epsilon_2$). This is done by measuring the ratio of the absorbance/path length at the first wavelength $(A/l)_1$ to the absorbance/path length at a second wavelength $(A/l)_2$ and equating this ratio to the ratios of the extinction coefficients: $(A/l)_1/(A/l)_2=\epsilon_1/\epsilon_2$.

The instruments and methods of the present invention also enable the user to measure the components in a complex mixture at the same time as long as the wavelengths that identify the multiple components in the sample can be separated. For example, a conventional spectrophotometer would not in a single experiment be able to determine the concentration of a sample where there are two components A, which is highly concentrated and absorbs predominantly at 300 nm and B which is quite dilute and absorbs at 600 nm. In a conventional spectrophotometer the measurement of the absorbance due to component B would preclude the measurement of the absorbance of component A as the concentration of A is high enough as to swamp the detector. The original sample would need to be diluted to determine component A, and in doing so component B would not produce enough signal to permit its concentration to be measured. In a conventional spectrophotometer the concentration of the components A and B cannot be measured simultaneously. In the present invention the path length can be altered so that both the concentration of components A and B can be determined together. Obviously, as long as there are peaks which uniquely identify a component within a sample the methods of the present invention can measure the concentration of the components of very complex samples. Additionally because the instrument is capable of generating data in real-time, the interaction of components within the sample can be monitored to produce kinetic data or any data for which a time course is required.

A better understanding of the present invention and of its many advantages will be had from the following examples, given by way of illustration.

EXAMPLES

Example 1

Measurement of Concentration of Camphor Sulphonic Acid

Camphor sulphonic acid (CSA) ((1S)-(+)-10 camphor sulfonic acid, Aldrich C2107-5G) is commonly used to check the calibration of circular dichroism instruments. It has a well defined absorbance peak at 285 nm with accepted absorbance 0.1486 A at 1 cm pathlength and 1 mg/mL.

Figure 6:
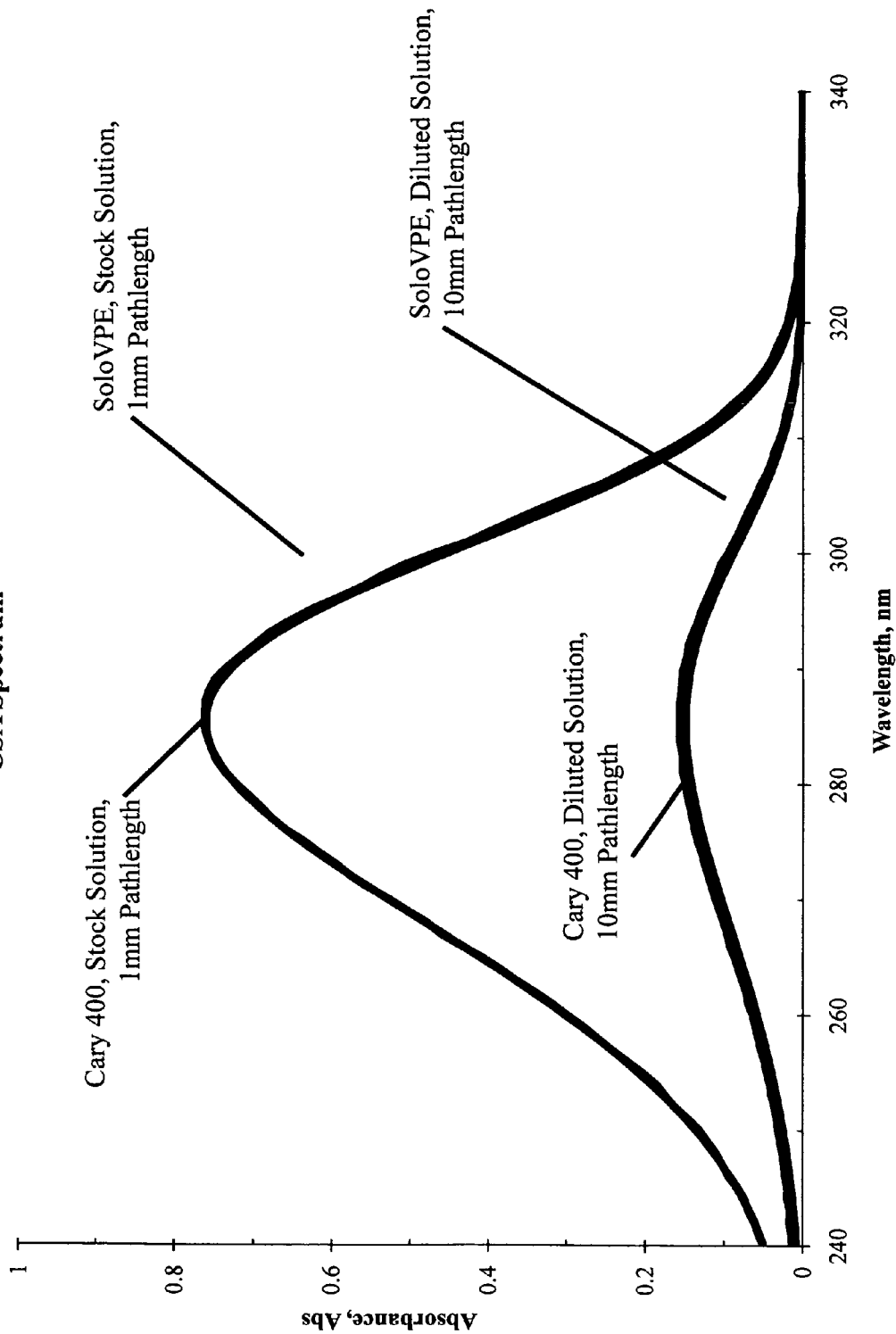
FIG. 6 shows the spectra of stock and diluted CSA from Cary400 and SoloVPE taken at a 1 mm and 10 mm path length

A stock CSA solution was prepared from 1.023 g CSA powder dissolved in 20 mL of distilled water to produce a solution of concentration of 51.15 mg/mL (0.2202M). This solution has a calculated absorbance 7.6001 Abs at 1 cm path length. A second CSA solution was prepared by diluting the stock CSA solution: 4.9 mL of stock was added to 245.1 mL of distilled water for a 250 mL total volume. This solution was filtered through 0.2µ nalgene filter. The concentration of the diluted solution is 1.00254 mg/mL (0.0043M). In FIG. 6 the spectra of both stock and diluted CSA solutions are shown. The spectra were taken at 1 mm and 10 mm path length by Cary400 (standard spectrophotometer) and one embodiment of the present invention (SoloVPE). In the case of the Cary 400 the stock and diluted CSA solution were transferred into cuvettes of path length 1 mm and 10 mm and placed into the Cary 400 for absorbance measurement. In the case of the SoloVPE is the path lengths of 1 mm and 10 mm were determined by computer control of the probe. The Spectra from SoloVPE shows highly consistance with the Cary 400. This

Example 2

Measurement of Concentration of Camphor Sulphonic Acid

Figure 7:
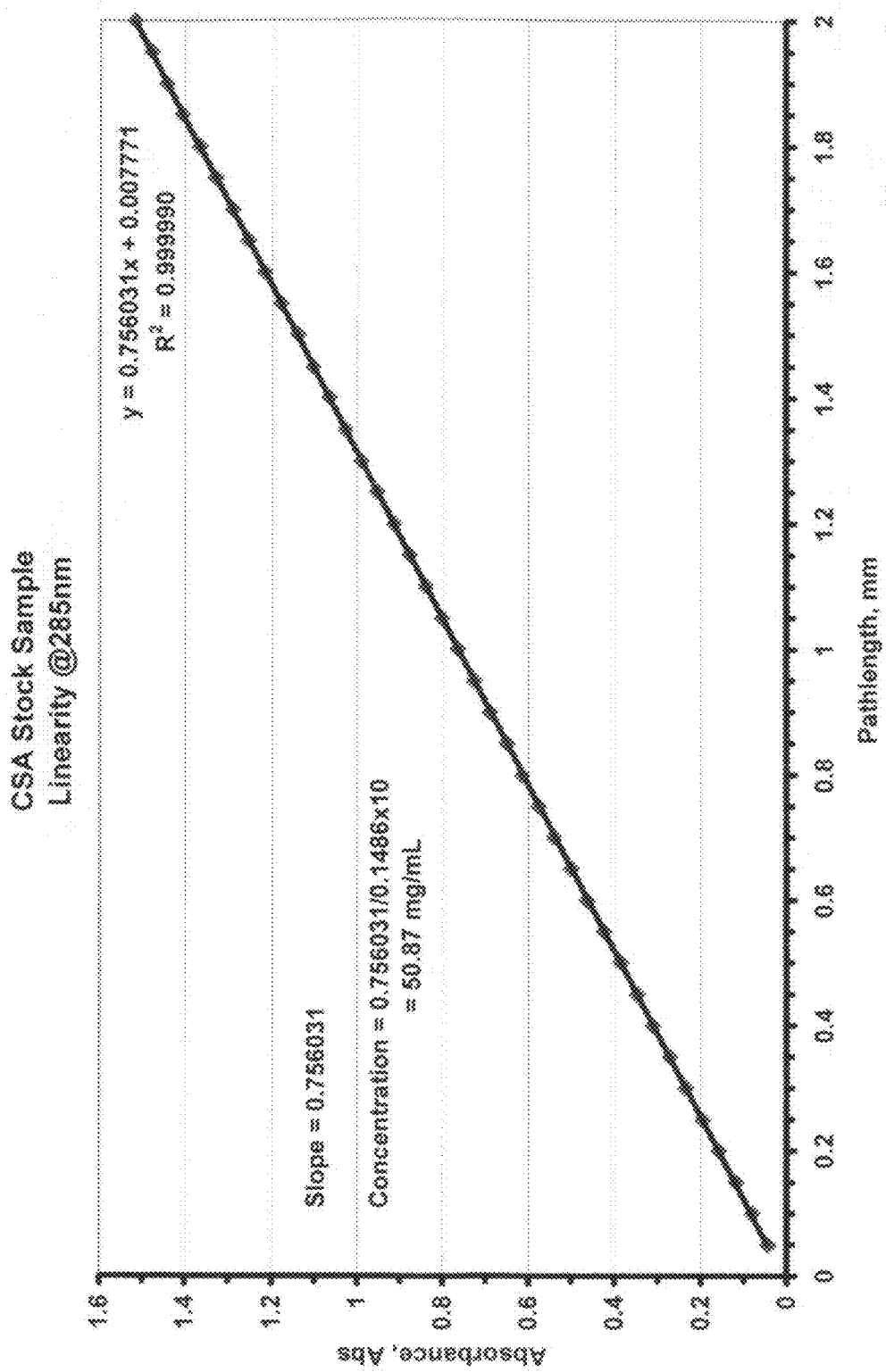
FIG. 7 shows the regression line of a plot of Absorbance at 285 nm versus path length for a stock solution of CSA.
Figure 8:
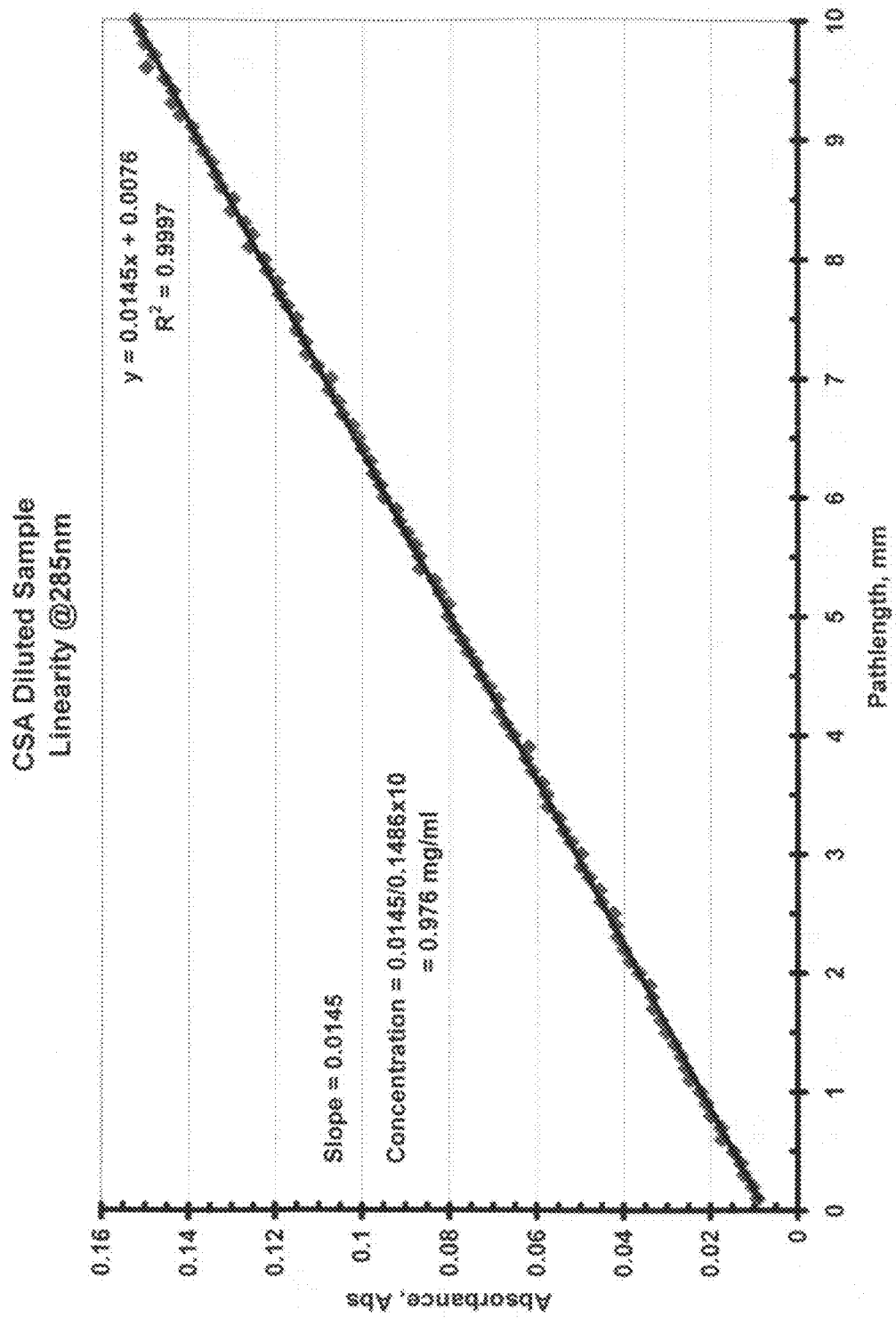
FIG. 8 shows the regression line of a plot of Absorbance at 285 nm versus path length for a diluted solution of CSA.

Stock CSA solution (as described in Example 1) was measured by an embodiment of the invention (SoloVPE) at 285 nm with path length varied from 0.05 mm to 2.0 mm in 0.05 mm increments. Diluted CSA solution (as described in Example 1) was measured by SoloVPE at 285 nm with path length varied from 1.0 mm to 10.0 mm in 0.1 mm increments. The experiment was repeated using a path length range of from 1 mm to 10 mm in 0.1 mm increments. The resulting regression lines from plots of the absorbance values versus the path length values are shown in FIGS. 2 and 3. These values are compared to a single reading at 285 nm in a Cary 400 spectrophotometer taken for the stock and diluted samples of CSA solution in a 10 mm cuvette. Using slope spectroscopy the sample concentration can be obtained from the linear regression curve of the absorbance vs. pathlength data. FIGS. 7 and 8 are the plots of absorbance vs. pathlength data from both stock and diluted solutions, respectively. The instrument (SoloVPE) measured the absorbances of stock solution with path lengths varied from 0.05 mm to 2.0 mm and diluted solution from 1 mm to 10 mm. The slope of linear regression curve for stock CSA solution is 0.756031 with linear correlation coefficient $R^2=0.99999$. The diluted CSA solution data has 0.0145 slope and $R^2=0.9997$. Based on the equation, Absorbance (A)/path length (l)=extinction coefficient ($\epsilon$)×concentration (c), slope values from the regression (A/l) were used to obtain the solution concentration. In this test, the concentration of stock solution is 50.88 mg/mL (0.219M) and diluted solution is 0.976 mg/mL (0.0042M). Compare with concentration values of the sample based on the composition of the samples from Example 1, the results obtained by the slope regression measurements at multiple path lengths have −0.53% and −2.6% difference for stock and diluted solutions respectively.

Example 3

Measurement of Wavelength Peaks at Multiple Path Lengths for Patent Blue

Figure 9:
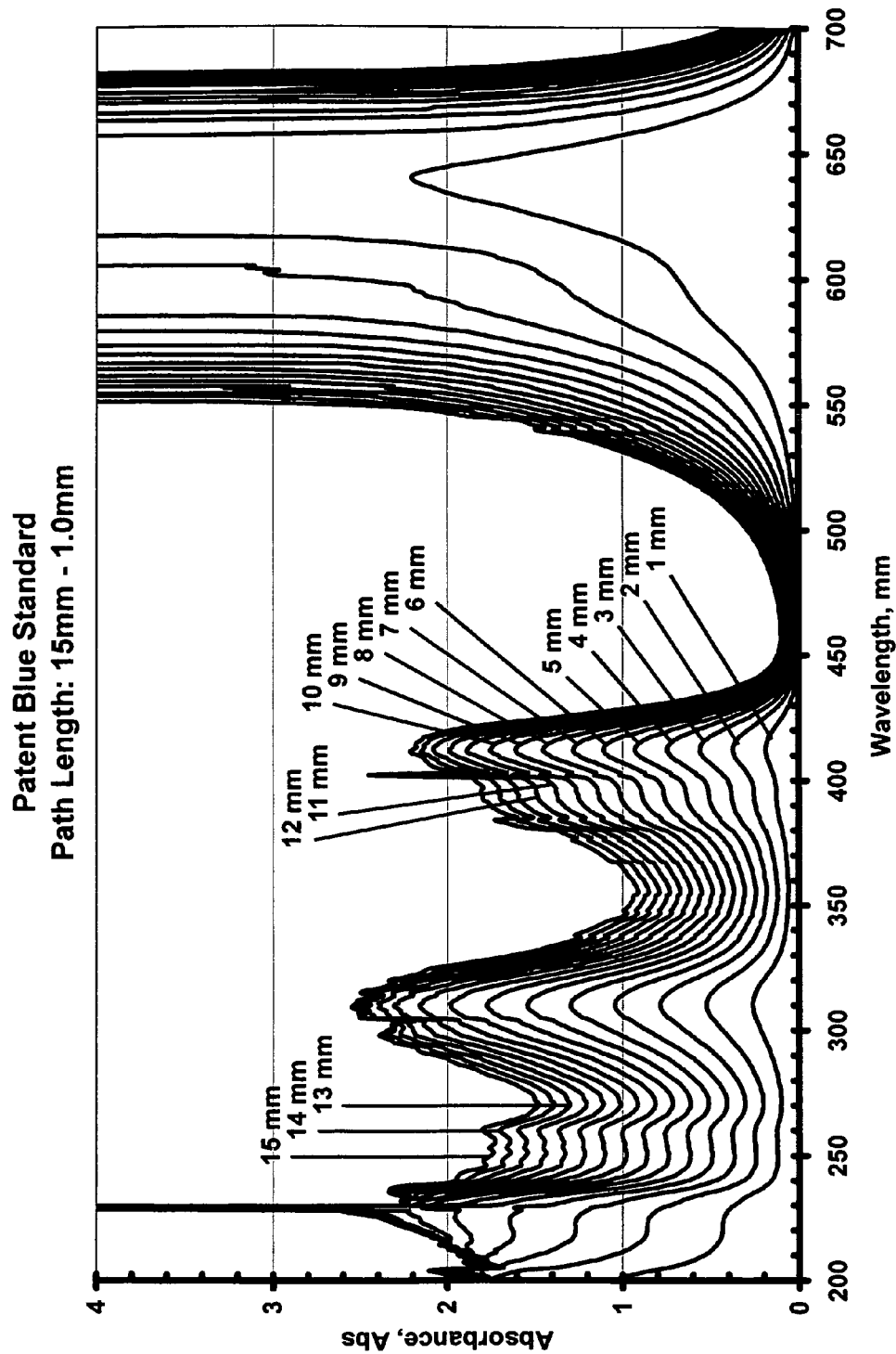
FIG. 9 is spectra of Patent Blue Standard at path lengths from 15.0 mm to 1.0 mm.

Patent Blue Standard was purchased from GFS Chemical, Inc., Columbus, Ohio. Patent Blue standard has absorbance peaks reported at 310 nm, 412 nm, and 639 nm wavelengths. In FIG. 9, the absorbance peaks at 310 nm and 412 nm can be easily identified in these path length scans. Even though both peaks can be seen in the plot, 412 nm peaks are already clearly defined at 15 mm path length while 310 nm peaks are noisy between 10-15 mm path lengths. This indicates that the signals at 310 nm wavelength close to the saturation level of the detector at the path lengths greater 10 mm. A clear 310 nm peak can be defined at path lengths greater than 10 mm. The 639 nm absorbance peak is absent in longer path lengths range and is not seen until the path length is reduced to about 1 mm.

Figure 10:
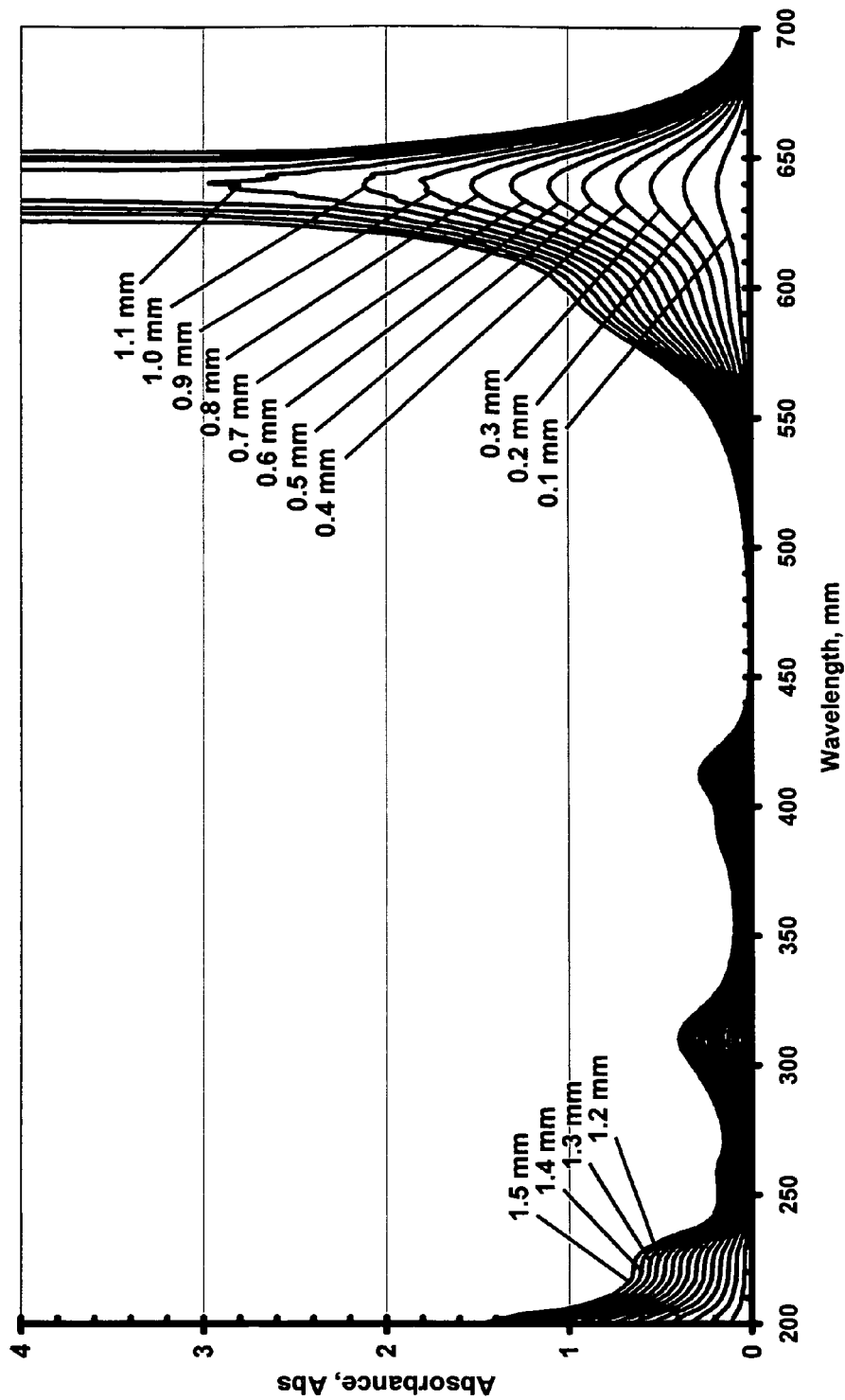
FIG. 10 is spectra of Patent Blue Standard at path lengths from 1.5 mm to 0.1 mm.

As the path lengths are reduced from 1.5 mm to 0.1 mm, (FIG. 10) the size of the three absorbance peaks is commensurately reduced. The absorbance peaks at 310 nm and 412 nm reached zero absorbance or detector noise level while the 639 nm absorbance peaks remain measurable and provide meaningful information. The data from FIGS. 9 and 10 were collected in one run from SoloVPE. For all commercial available spectrophotometers, one has to take several steps, such as diluting samples and changing different sizes of cuvette, to obtain same results.

Example 4

Measurement of Concentrated Bovine Serum Albumin

Figure 11:
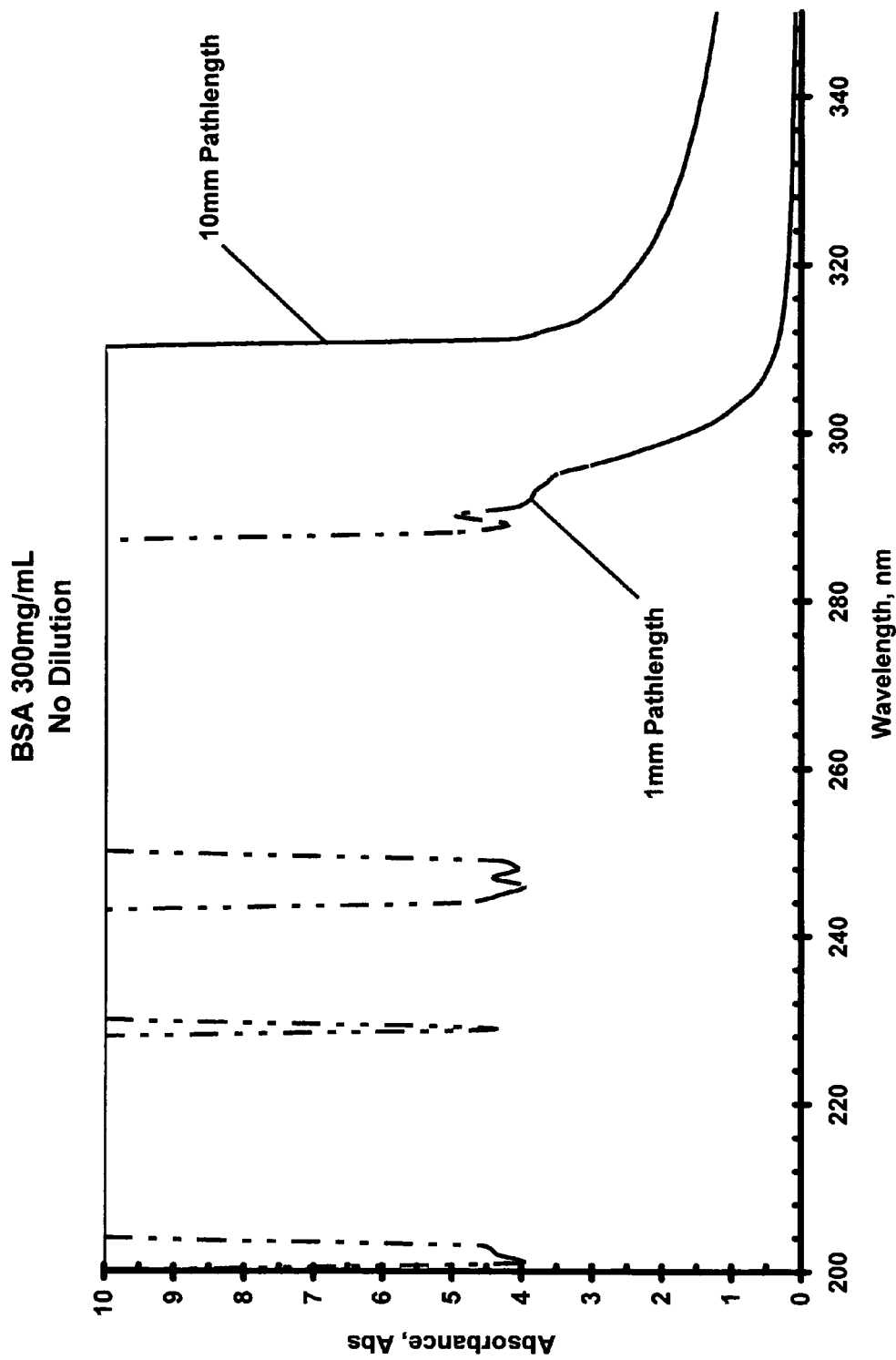
FIG. 11 is the spectra of BSA from 200 to 340 nm at 10 min and 1 mm path length on a standard spectrophotometer.
Figure 12:
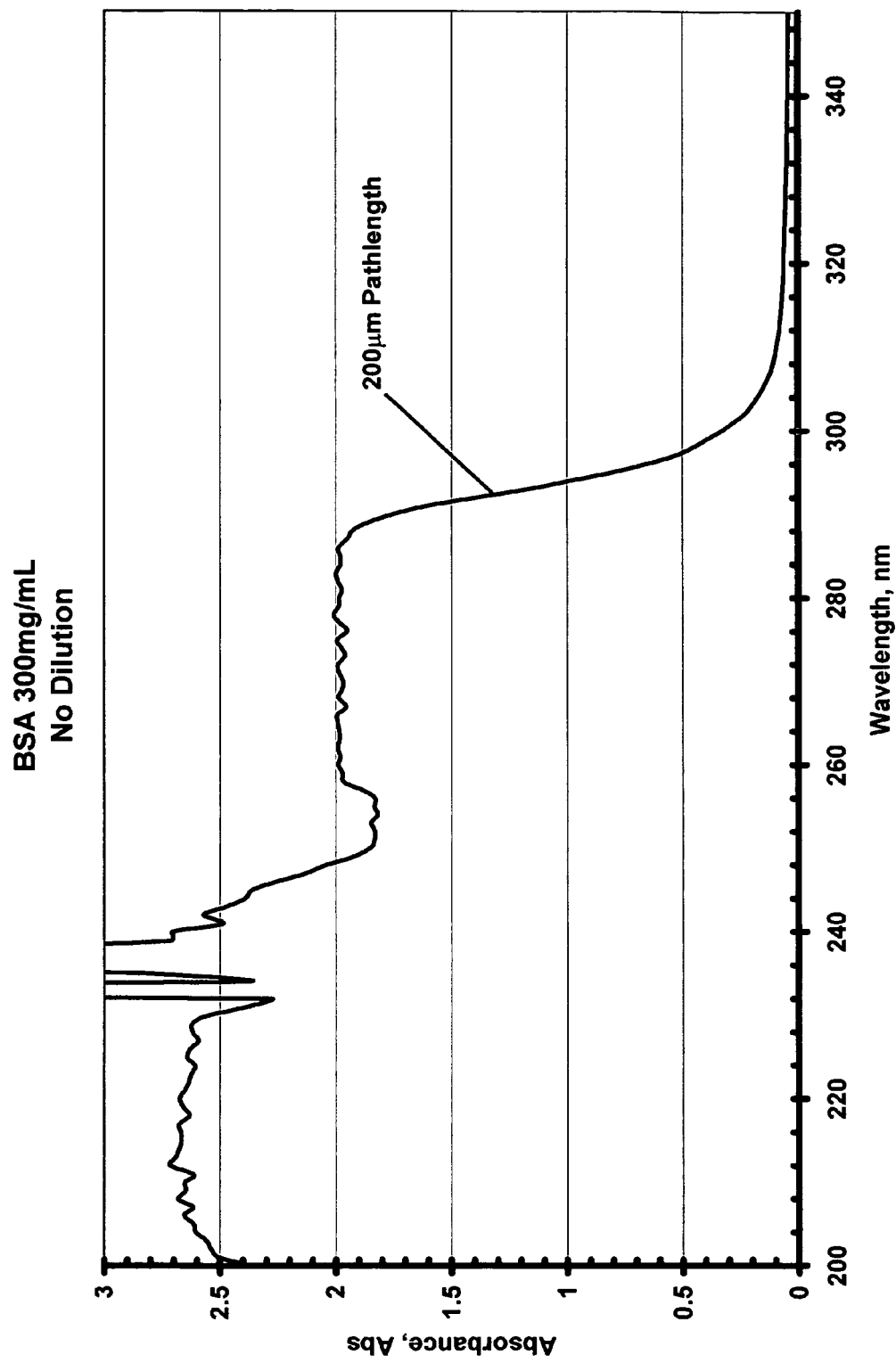
FIG. 12 is the spectra of BSA from 200 to 340 nm at 200 μm path length

BSA solution was purchased from Sigma-Aldrich Co., P/N A7284 300 mg/mL. BSA sample has optical absorbance 0.667 Abs at 279 nm for 1 gm/L concentration. In this example, the concentration of BSA is 300 mg/mL±10% error according to the data provided by Sigma-Aldrich. The absorbance scans of this BSA solution in 10 mm and 1 mm cuvettes from Cary 50 Spectrophotometer are shown in FIG. 11. Both absorbance values at 279 nm saturate the detector because of the high concentration of the solution. FIG. 12 is the absorbance scan of same solution at 200 μm path length using an instrument of the present invention. This scan demonstrates that the absorbance value at this small path length (smallest commercially available cuvette) also saturates the detector. FIG. 13 is the spectra of the BSA solution taken by the SoloVPE instrument at 0.1 mm to 0.01 mm path lengths with 0.005 mm steps. In the tested path lengths range, the absorbance peak at 279 nm wavelength does not saturate the detector. Collecting absorbance values at 279 nm of each path lengths, a plot of the absorbance vs. path length (FIG. 14) and regression analysis yields a concentration of the BSA solution of 330.6 mg/mL.

While the present invention has been described in terms of the preferred embodiments, it is understood that variations and modifications will occur to those skilled in the art. Therefore, it is intended that the appended claims cover all such equivalent variations that come within the scope of the invention as claimed.

We claim:

1. A method of determining the concentration of a sample comprising:
   (a) placing the sample solution in a vessel;
   (b) placing a probe within sample;
   (c) taking an absorbance reading;
   (d) moving the probe relative to the vessel with a unidirectional sliding mechanism by a predetermined increment such that a preselected path length through the solution is obtained such that a preselected path length through the solution is obtained and taking an absorbance reading at a predetermined wavelength;
   (e) repeating steps (c) and (d) sequentially one or more times;
   (f) generating a regression line from the absorbance values and path length such that a slope of the regression line is obtained; and,
   (g) determining the concentration of the sample by dividing the slope of the regression line by the extinction coefficient of the sample.

2. A method of determining the concentration of a sample comprising:
   (a) placing the sample solution in a vessel;
   (b) moving a probe relative to the vessel such that the probe makes contact with the bottom of the vessel;
   (c) moving the probe relative to the vessel with a unidirectional sliding mechanism such that the probe moves from the bottom of the vessel through the sample by a predetermined increment such that a preselected path length through the solution is obtained;

(d) taking an absorbance reading at a predetermined wavelength;

(e) repeating steps (c) and (d) sequentially one or more times;

(f) generating a regression line from the absorbance and path length such that a slope of the regression line is obtained; and, (g) determining the concentration of the sample by dividing the slope of the regression line by the extinction coefficient of the sample.

3. The method of claim 1 wherein the predetermine increment is the same for each iteration.

4. The method of claim 1 wherein the predetermined increment is from about 0.005 mm to about 50 mm.

5. The method of claim 1 wherein the predetermined increment is from about 0.0002 mm to about 10 mm.

6. The method of claim 2 wherein the predetermine increment is the same for each iteration.

7. The method of claim 2 wherein the predetermined increment is from about 0.005 mm to about 50 mm.

8. The method of claim 2 wherein the predetermined increment is from about 0.0002 mm to about 10 mm.

9. The method of claim 1 wherein the regression line has an $R^2$ value of from around 0.99950 to about 0.99999.

10. The method of claim 2 wherein the regression line has an $R^2$ value of from around 0.99950 to about 0.9999.

11. The method of claim 1 wherein the regression line has an $R^2$ value of from around 0.99990 to about 0.99999.

12. The method of claim 2 wherein the regression line has an $R^2$ value of from around 0.99990 to about 0.99999.

13. An instrument for determine the concentration of a sample at multiple path lengths comprising:

(a) a light source operably linked to a probe;

(b) a sample vessel that can contain the sample;

(c) a motor operably linked to the sample vessel such that the sample vessel can be moved relative to the probe to provide variable path lengths;

(d) a probe that can carry electromagnetic radiation that can be moved relative to the sample vessel by the motor;

(e) a unidirectional sliding mechanism operably linked to the probe;

(f) a detector located below the sample vessel that can detect electromagnetic radiation disposed such that the detector is substantially perpendicular to the electromagnetic radiation emanating from the probe and such that the electromagnetic radiation moves through the sample and is detected by the detector; and, (g) software for calculating the concentration of the sample based on the information provided by the detector at the predetermined path lengths;

comprising generating a regression line from the absorbance and path length such that a slope of the regression line is obtained; and determining the concentration of the sample by dividing the slope of the regression line by the extinction coefficient of the sample.

14. The instrument of claim 13, wherein the unidirectional sliding mechanism is passively locked.

15. The instrument of claim 13, wherein the unidirectional sliding mechanism is actively locked by a user.

16. The instrument of claim 13, wherein the unidirectional sliding mechanism is operably linked to the probe.

17. The instrument of claim 13, wherein the unidirectional sliding mechanism is operably linked to the sample vessel.

18. The instrument of claim 13, wherein the path lengths are between about 0.2 µm to about 1.0 µm.

19. The instrument of claim 13, wherein the path lengths are between about 0.2 µm to about 1.0 µm.

20. The instrument of claim 13, wherein the motor is operably linked to the sample vessel though a sample vessel stage.

21. The instrument of claim 13, wherein the motor is computer controlled.

22. The instrument of claim 13, wherein the software can calculate the concentration based on deriving the slope of a line based on the ratio of path length to absorbance values.

23. The instrument of claim 22, wherein the slope of the line is derived while the values are being measured.

* * * * *